United States Patent
Hossainy et al.

(10) Patent No.: US 6,641,607 B1
(45) Date of Patent: Nov. 4, 2003

(54) DOUBLE TUBE STENT

(75) Inventors: Syed F. A. Hossainy, Fremont, CA (US); Shamim M. Malik, Temecula, CA (US); Steven Wu, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 183 days.

(21) Appl. No.: 09/753,294

(22) Filed: Dec. 29, 2000

(51) Int. Cl.⁷ .................................................. A61F 2/06
(52) U.S. Cl. ...................... 623/1.15; 623/1.44; 623/1.42
(58) Field of Search ................ 623/1.13, 1.15, 623/1.16, 1.34, 1.14, 1.18–1.22

(56) References Cited

U.S. PATENT DOCUMENTS

| | | |
|---|---|---|
| 3,105,492 A | 10/1963 | Jeckel |
| 3,868,956 A | 3/1975 | Alfidi et al. |
| 3,993,078 A | 11/1976 | Bergentz et al. |
| 4,130,904 A | 12/1978 | Whalen |
| 4,718,907 A | 1/1988 | Karwoski et al. |
| 4,816,339 A | 3/1989 | Tu et al. |
| 4,879,135 A | 11/1989 | Greco et al. |
| 4,892,539 A | 1/1990 | Koch |
| 4,902,289 A | 2/1990 | Yannas |
| 4,986,831 A | 1/1991 | King et al. |
| 5,024,671 A | 6/1991 | Tu et al. |
| 5,037,377 A | 8/1991 | Alonso |
| 5,047,050 A | 9/1991 | Arpesani |
| 5,059,166 A | 10/1991 | Fischell et al. |
| 5,062,829 A | 11/1991 | Pryor et al. |
| 5,064,435 A * | 11/1991 | Porter ........................ 623/23.7 |
| 5,078,736 A | 1/1992 | Behl |
| 5,084,065 A | 1/1992 | Weldon et al. |
| 5,100,429 A | 3/1992 | Sinofsky et al. |
| 5,104,403 A | 4/1992 | Brotzu et al. |
| 5,116,360 A | 5/1992 | Pinchuk et al. |
| 5,156,623 A | 10/1992 | Hakamatsuka et al. |
| 5,163,951 A | 11/1992 | Pinchuk et al. |
| 5,163,958 A | 11/1992 | Pinchuk |
| 5,176,617 A | 1/1993 | Fischell et al. |
| 5,180,366 A | 1/1993 | Woods |
| 5,192,311 A | 3/1993 | King et al. |
| 5,197,977 A | 3/1993 | Hoffman, Jr. et al. |
| 5,234,457 A | 8/1993 | Andersen |
| 5,236,446 A | 8/1993 | Dumon |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,302,168 A | 4/1994 | Hess |
| 5,354,329 A | 10/1994 | Whalen |
| 5,356,433 A | 10/1994 | Rowland et al. |
| 5,370,682 A | 12/1994 | Schmitt |
| 5,380,299 A | 1/1995 | Fearnot et al. |
| 5,382,259 A | 1/1995 | Phelps et al. |

(List continued on next page.)

FOREIGN PATENT DOCUMENTS

WO     WO 98/23228     6/1998

*Primary Examiner*—David H. Willse
*Assistant Examiner*—Hieu Phan
(74) *Attorney, Agent, or Firm*—Fulwider Patton Lee & Utecht, LLP

(57) ABSTRACT

A stent or intraductal medical device manufactured from a tubular member having an inner tube tightly fitted into an outer tube is provided. Microdepots may be formed on the outer surface of the inner tube, and may contain radioactive, radiopaque or therapeutic substances. A method for manufacturing such a medical device or stent is also described. The material to be deposited on the inner tube may be deposited on the inner tube by dipping or immersion, or the material may be applied to the inner tube using micro-injection or electrodeposition. The material to be deposited may be applied to cavities or microdepots formed in the outer surface of the inner tube. Excess material may be removed from the inner tube by centrifugation or shaking, and the material to be deposited may be heated to bond the material to the surface of the microdepots on the inner tube.

21 Claims, 4 Drawing Sheets

U.S. PATENT DOCUMENTS

| | | |
|---|---|---|
| 5,383,927 A | 1/1995 | De Goicoechea et al. |
| 5,411,550 A | 5/1995 | Herweck et al. |
| 5,413,597 A | 5/1995 | Krajicek |
| 5,415,619 A | 5/1995 | Lee et al. |
| 5,419,760 A | 5/1995 | Narciso, Jr. |
| 5,443,458 A | 8/1995 | Eury |
| 5,443,496 A | 8/1995 | Schwartz et al. |
| 5,449,382 A | 9/1995 | Dayton |
| 5,464,419 A | 11/1995 | Glastra |
| 5,464,438 A | 11/1995 | Menaker |
| 5,464,450 A | 11/1995 | Buscemi et al. |
| 5,476,509 A | 12/1995 | Keogh et al. |
| 5,499,995 A | 3/1996 | Teirstein |
| 5,500,013 A | 3/1996 | Buscemi et al. |
| 5,507,770 A | 4/1996 | Turk |
| 5,522,882 A | 6/1996 | Gaterud et al. |
| 5,527,353 A | 6/1996 | Schmitt |
| 5,534,024 A | 7/1996 | Rogers et al. |
| 5,549,663 A | 8/1996 | Cottone, Jr. |
| 5,549,664 A | 8/1996 | Hirata et al. |
| 5,551,954 A | 9/1996 | Buscemi et al. |
| 5,554,180 A | 9/1996 | Turk |
| 5,554,182 A | 9/1996 | Dinh et al. |
| 5,556,414 A | 9/1996 | Turi |
| 5,562,727 A | 10/1996 | Turk et al. |
| 5,571,166 A | 11/1996 | Dinh et al. |
| 5,571,170 A | 11/1996 | Palmaz et al. |
| 5,571,171 A | 11/1996 | Barone et al. |
| 5,571,173 A | 11/1996 | Parodi |
| 5,575,818 A | 11/1996 | Pinchuk |
| 5,578,071 A | 11/1996 | Parodi |
| 5,578,072 A | 11/1996 | Barone et al. |
| 5,578,075 A | 11/1996 | Dayton |
| 5,599,352 A | 2/1997 | Dinh et al. |
| 5,607,442 A | 3/1997 | Fischell et al. |
| 5,607,468 A | 3/1997 | Rogers et al. |
| 5,609,629 A | 3/1997 | Fearnot et al. |
| 5,624,411 A | 4/1997 | Tuch |
| 5,626,611 A | 5/1997 | Liu et al. |
| 5,628,786 A | 5/1997 | Banas et al. |
| 5,628,787 A | 5/1997 | Mayer |
| 5,628,788 A | 5/1997 | Pinchuk |
| 5,629,077 A | 5/1997 | Turnlund et al. |
| 5,630,840 A | 5/1997 | Mayer |
| 5,632,776 A | 5/1997 | Kurumatani et al. |
| 5,632,840 A | 5/1997 | Campbell |
| 5,637,113 A | 6/1997 | Tartaglia et al. |
| 5,645,559 A | 7/1997 | Hachtman et al. |
| 5,649,951 A | 7/1997 | Davidson |
| 5,649,977 A | 7/1997 | Campbell |
| 5,651,174 A | 7/1997 | Schwartz et al. |
| 5,665,114 A | 9/1997 | Weadock et al. |
| 5,674,241 A | 10/1997 | Bley et al. |
| 5,674,277 A | 10/1997 | Freitag |
| 5,679,400 A | 10/1997 | Tuch |
| 5,681,345 A | 10/1997 | Euteneuer |
| 5,683,448 A | 11/1997 | Cragg |
| 5,685,306 A | 11/1997 | Davidson |
| 5,690,670 A | 11/1997 | Davidson |
| 5,693,085 A | 12/1997 | Buirge et al. |
| 5,697,967 A | 12/1997 | Dinh et al. |
| 5,700,285 A | 12/1997 | Myers et al. |
| 5,700,287 A | 12/1997 | Myers et al. |
| 5,707,385 A | 1/1998 | Williams |
| 5,711,763 A | 1/1998 | Nonami et al. |
| 5,713,949 A | 2/1998 | Jayaraman |
| 5,716,394 A | 2/1998 | Bruchman et al. |
| 5,716,660 A | 2/1998 | Weadock et al. |
| 5,718,723 A | 2/1998 | Matsuda et al. |
| 5,718,726 A | 2/1998 | Amon et al. |
| 5,723,004 A | 3/1998 | Dereume et al. |
| 5,725,567 A | 3/1998 | Wolff et al. |
| 5,725,570 A | 3/1998 | Heath |
| 5,725,572 A | 3/1998 | Lam et al. |
| 5,733,327 A | 3/1998 | Igaki et al. |
| 5,735,892 A | 4/1998 | Myers et al. |
| 5,735,897 A | 4/1998 | Buirge |
| 5,741,324 A | 4/1998 | Glastra |
| 5,741,325 A | 4/1998 | Chaikof et al. |
| 5,741,327 A | 4/1998 | Frantzen |
| 5,749,880 A | 5/1998 | Banas et al. |
| 5,755,774 A | 5/1998 | Pinchuk |
| 5,766,710 A | 6/1998 | Turnlund et al. |
| 5,776,184 A | 7/1998 | Tuch |
| 5,779,729 A | 7/1998 | Severini |
| 5,782,908 A | 7/1998 | Cahalan et al. |
| 5,782,910 A | 7/1998 | Davidson |
| 5,800,511 A | 9/1998 | Mayer |
| 5,800,512 A | 9/1998 | Lentz et al. |
| 5,814,063 A | 9/1998 | Freitag |
| 5,824,038 A | 10/1998 | Wall |
| 5,824,042 A | 10/1998 | Lombardi et al. |
| 5,824,043 A | 10/1998 | Cottone, Jr. |
| 5,824,045 A | 10/1998 | Alt |
| 5,824,049 A | 10/1998 | Ragheb et al. |
| 5,824,050 A | 10/1998 | Karwoski et al. |
| 5,824,056 A | 10/1998 | Rosenberg |
| 5,824,077 A | 10/1998 | Mayer |
| 5,827,327 A | 10/1998 | McHaney et al. |
| 5,837,008 A | 11/1998 | Berg et al. |
| 5,843,089 A | 12/1998 | Sahatjian et al. |
| 5,843,161 A | 12/1998 | Solovay |
| 5,843,166 A | 12/1998 | Lentz et al. |
| 5,843,172 A | 12/1998 | Yan |
| 5,851,217 A | 12/1998 | Wolff et al. |
| 5,851,230 A | 12/1998 | Weadock et al. |
| 5,851,231 A | 12/1998 | Wolff et al. |
| 5,851,232 A | 12/1998 | Lois |
| 5,871,436 A | 2/1999 | Eury |
| 5,871,437 A | 2/1999 | Alt |
| 5,871,535 A | 2/1999 | Wolff et al. |
| 5,871,538 A | 2/1999 | Dereume |
| 5,876,433 A | 3/1999 | Lunn |
| 5,882,335 A | 3/1999 | Leone et al. |
| 5,891,191 A | 4/1999 | Stinson |
| 5,895,407 A | 4/1999 | Jayaraman |
| 5,897,587 A | 4/1999 | Martakos et al. |
| 5,897,589 A | 4/1999 | Cottenceau et al. |
| 5,899,935 A | 5/1999 | Ding |
| 5,902,266 A | 5/1999 | Leone et al. |
| 5,911,753 A | 6/1999 | Schmitt |
| 5,916,264 A | 6/1999 | Von Oepen et al. |
| 5,919,126 A | 7/1999 | Armini |
| 5,925,075 A | 7/1999 | Myers et al. |
| 5,928,279 A | 7/1999 | Shannon et al. |
| 5,951,586 A | 9/1999 | Berg et al. |
| 5,954,693 A | 9/1999 | Barry |
| 5,957,974 A | 9/1999 | Thompson et al. |
| 5,961,545 A | 10/1999 | Lentz et al. |
| 5,968,070 A | 10/1999 | Bley et al. |
| 5,968,091 A | 10/1999 | Pinchuk et al. |
| 5,972,027 A | 10/1999 | Johnson |
| 5,976,169 A | 11/1999 | Imran |
| 5,980,551 A | 11/1999 | Summers et al. |
| 5,980,565 A | 11/1999 | Jayaraman |
| 5,980,566 A | 11/1999 | Alt et al. |
| 5,993,489 A | 11/1999 | Lewis et al. |
| 5,997,468 A | 12/1999 | Wolff et al. |
| 6,001,125 A | 12/1999 | Golds et al. |

| | | |
|---|---|---|
| 6,004,346 A | 12/1999 | Wolff et al. |
| 6,004,348 A * | 12/1999 | Banas et al. ................ 606/198 |
| 6,010,445 A | 1/2000 | Armini et al. |
| 6,010,529 A | 1/2000 | Herweck et al. |
| 6,013,099 A | 1/2000 | Dinh et al. |
| 6,015,430 A | 1/2000 | Wall |
| 6,015,431 A | 1/2000 | Thornton et al. |
| 6,022,374 A | 2/2000 | Imran |
| 6,036,724 A | 3/2000 | Lentz et al. |
| 6,036,725 A | 3/2000 | Avellanet |
| 6,039,755 A | 3/2000 | Edwin et al. |
| 6,039,757 A | 3/2000 | Edwards et al. |
| 6,042,605 A | 3/2000 | Martin et al. |
| 6,048,360 A | 4/2000 | Khosravi et al. |
| 6,053,943 A | 4/2000 | Edwin et al. |
| 6,063,101 A | 5/2000 | Jacobsen et al. |
| 6,063,111 A | 5/2000 | Hieshima et al. |
| 6,063,112 A | 5/2000 | Sgro |
| 6,071,305 A | 6/2000 | Brown et al. |
| 6,071,307 A | 6/2000 | Rhee et al. |
| 6,077,296 A | 6/2000 | Shokoohi et al. |
| 6,086,610 A | 7/2000 | Duerig et al. |
| 6,090,135 A | 7/2000 | Plaia et al. |
| 6,099,557 A | 8/2000 | Schmitt |
| 6,099,559 A | 8/2000 | Nolting |
| 6,099,561 A | 8/2000 | Alt |
| 6,102,943 A | 8/2000 | McGuinness |
| 6,106,454 A | 8/2000 | Berg et al. |
| 6,117,168 A | 9/2000 | Yang et al. |
| 6,120,536 A | 9/2000 | Ding et al. |
| 6,132,461 A | 10/2000 | Thompson |
| 6,139,573 A | 10/2000 | Sogard et al. |
| 6,143,022 A | 11/2000 | Shull et al. |
| 6,149,681 A | 11/2000 | Houser et al. |
| 6,152,869 A | 11/2000 | Park et al. |
| 6,156,064 A | 12/2000 | Chouinard |
| 6,159,142 A | 12/2000 | Alt |
| 6,162,244 A | 12/2000 | Braun et al. |
| 6,165,211 A | 12/2000 | Thompson |
| 6,165,212 A | 12/2000 | Dereume et al. |
| 6,174,326 B1 | 1/2001 | Kitaoka et al. |
| 6,254,632 B1 * | 7/2001 | Wu et al. .................. 623/1.15 |
| 6,273,908 B1 * | 8/2001 | Ndondo-Lay ............... 606/194 |
| 6,379,381 B1 * | 4/2002 | Hossainy et al. .......... 623/1.15 |
| 6,425,855 B2 | 7/2002 | Tomonto |

* cited by examiner

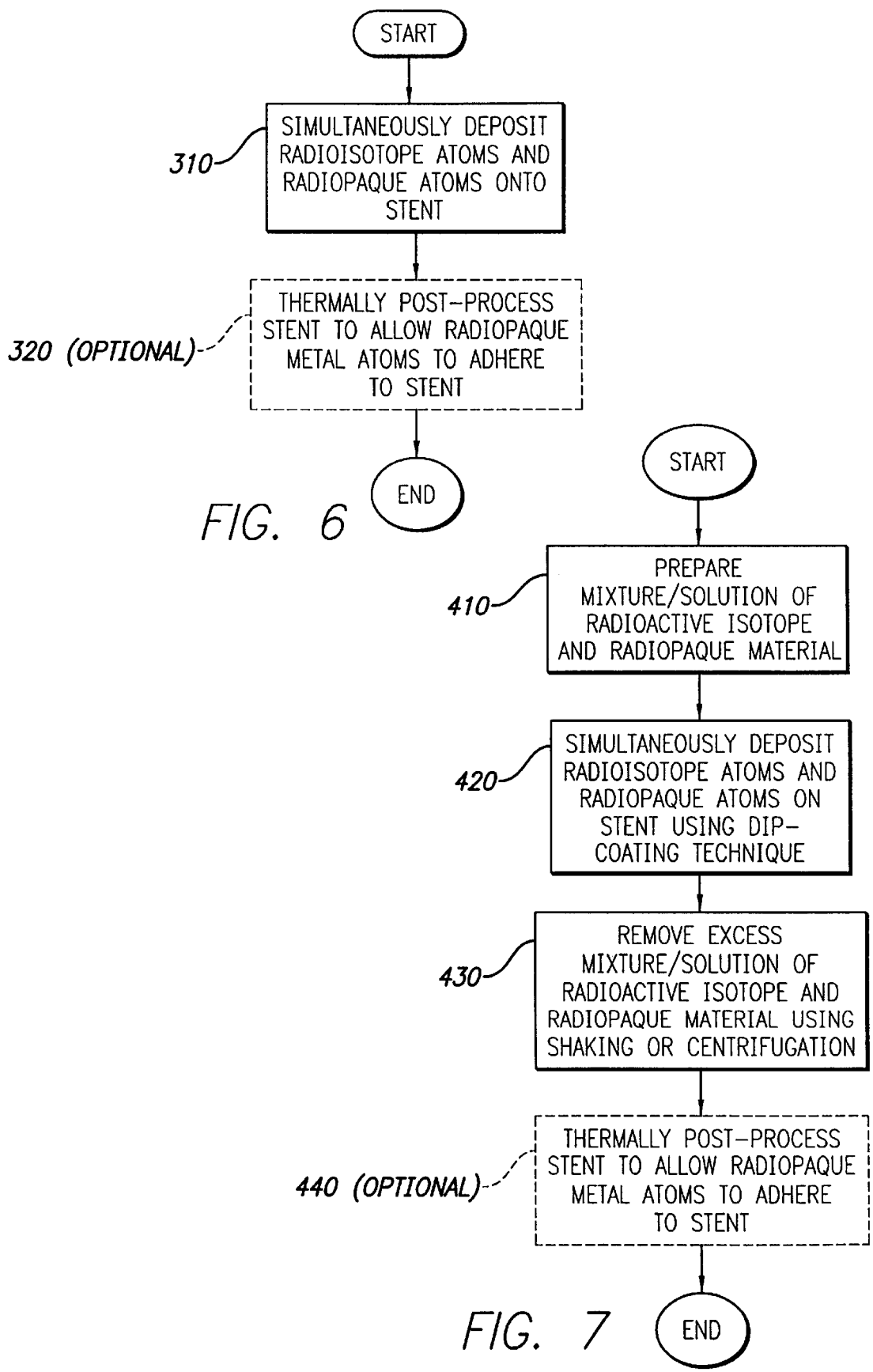

DOUBLE TUBE STENT

BACKGROUND OF THE INVENTION

1. Field of the Invention

The present invention relates generally to implantable medical devices and to a method for manufacturing implantable medical devices and depositing and affixing solids onto those devices. More particularly, the present invention relates to an implantable medical device, such as a stent or other intravascular or intraductal medical device, and to a method for depositing and affixing radiopacifiers, radioactive isotopes and or therapeutical chemicals or drugs onto those devices.

2. Description of Related Art

In a typical percutaneous transluminal coronary angioplasty (PTCA) for compressing lesion plaque against the artery wall to dilate the artery lumen, a guiding catheter is percutaneously introduced into the cardiovascular system of a patient through the brachial or femoral arteries and advanced through the vasculature until the distal end is in the ostium. A dilatation catheter having a balloon on the distal end is introduced through the catheter. The catheter is first advanced into the patient's coronary vasculature until the dilatation balloon is properly positioned across the lesion.

Once in position across the lesion, a flexible, expandable, preformed balloon is inflated to a predetermined size at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty.

In angioplasty procedures of the kind referenced above, restenosis of the artery often develops which may require another angioplasty procedure, a surgical bypass operation, or some method of repairing or strengthening the area. To reduce the likelihood of the development of restenosis and strengthen the area, a physician can implant an intravascular prosthesis, typically called a stent, for maintaining vascular patency. A stent is a device used to hold tissue in place or to provide a support for a vessel to hold it open so that blood flows freely. Statistical data suggests that with certain stent designs, the restenosis rate is significantly less than the overall restenosis rate for non-stented arteries receiving a PTCA procedure.

A variety of devices are known in the art for use as stents, including expandable tubular members, in a variety of patterns, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery at the lesion. The stent is then expanded to a larger diameter, by the balloon portion of the catheter, to implant the stent in the artery at the lesion. Typical stents and stent delivery systems are more fully disclosed in U.S. Pat. No. 5,514,154 (Lau et al.), U.S. Pat. No. 5,507,768 (Lau et al.), and U.S. Pat. No. 5,569,295 (Lam et al.).

Stents are commonly designed for long-term implantation within the body lumen. Some stents are designed for non-permanent implantation within the body lumen. By way of example, several stent devices and methods can be found in commonly assigned and common owned U.S. Pat. No. 5,002,560 (Machold et al.), U.S. Pat. No. 5,180,368 (Garrison), and U.S. Pat. No. 5,263,963 (Garrison et al.).

Patients treated by PTCA procedures, even when implanted with stents, however, may suffer from restenosis, at or near the original site of the stenosis, the coronary vessel collapsing or becoming obstructed by extensive tissue growth, also known as intimal hyperplasia. Clinical studies have indicated that anti-proliferative drug therapy or intravascular low-dose radiation therapy after balloon angioplasty or an atherectomy procedure can prevent or reduce the rate of restenosis caused by intimal hyperplasia.

One approach for performing low-dose intravascular radiotherapy is using a treatment catheter with a low-intensity radiation source. Another approach uses a low-intensity implantable radioactive device such as a radioactive stent with either beta emitting or low energy gamma-emitting radioisotopes. Yet another approach contemplates treating the area of the stenosis over an extended period of time with low dosages of anti-proliferative chemicals or drug compounds.

Intravascular or intraductal implantation of a stent generally involves advancing the stent on a balloon catheter or a similar device to the designated vessel/duct site, properly positioning the stent at the vessel/duct site, and deploying the stent by inflating the balloon which then expands the stent radially against the wall of the vessel/duct. Proper positioning of the stent requires precise placement of the stent at the vessel/duct site to be treated. Visualizing the position and expansion of the stent within a vessel/duct area is usually done using a fluoroscopic or x-ray imaging system.

Where the area of a lesion is to be treated with radiation, the implantable stent is generally made radioactive prior to being inserted into the patient. To make a stent radioactive, a number of techniques are used in the field. For example, a beta-emitting or low energy gamma-emitting radioisotope may be implanted or alloyed into a metal from which the stent is made. The radioisotope may also be coated onto the surface of the stent using an electroplating process. Furthermore, the stent may be made radioactive through neutron activation in a nuclear reactor or similar facility.

Each of these techniques has certain disadvantages including poor and/or non-uniform adhesion of the radioisotope to the surface of the stent, fabrication difficulties with respect to radiation exposure of workers during the manufacturing process, and the risk of generating considerable quantities of undesired isotopes from the neutron activation process which may continue to affect the irradiated tissue long after the desired restenosis treatment period is over. Another significant shortcoming associated with current methods of making a stent radioactive is that these methods are complex and require the performance of many sequential processing steps, which greatly increase the radioactive stent manufacturing cost.

Where the area of the lesion is to be treated using anti-proliferative chemicals or drug compounds, the stent must be coated with the chemical or drug prior to implantation. Such coatings may make the stent difficult to handle, and may complicate implantation of the stent. Further, variations in the thickness of the coating may provide for varying release of the chemical or drug at the lesion site, possible affecting the efficacy of the anti-proliferative effect on the surrounding tissue.

A requirement for any clinically useful stent is that it should have good visibility under fluoroscopic x-ray illumination so that the position of the stent during the implantation procedure is visible to the physician performing the procedure. Since implantable radioactive stents are generally made of metal or metal alloys such as 316L stainless steel or nickel-titanium alloy, such as nitinol, they are not readily visible under fluoroscopic illumination. To make these, and other, non-radioactive, stents manufactured from non-radiopaque materials visible in an x-ray, radiopaque markers are typically attached onto the stent using a number of techniques. One current technique involves applying a coating of a radiopaque marker material, also called radiopacifier material such as gold or tantalum onto the stent, or selected portions of the stent, using an electroplating process. Another technique involves soldering or brazing a radiopaque marker material at specific locations onto the stent. Generally, radiopaque markers are soldered at the longitudinal ends, that is, the most proximal and most distal portions of the stent.

A number of shortcomings or disadvantages are associated with the prior art devices and techniques for attaching radiopaque markers, radioisotopes and chemicals or drugs onto stents or other implantable medical devices. For example, certain conventional radiopaque markers attached onto a stent tend to protrude from the walls of the stent, thus altering the stent profile under fluoroscopy. Other current radiopaque markers that are attached within the surface of the stent may impair the expansion capability of the stent. Still other current methods of attaching radiopaque markers or radioisotopes to the surface of a stent are disadvantageous in that some radiopaque materials and radioisotopes are not compatible with body fluids or tissue and thus must be covered by another material, such as stainless steel, that is compatible with body fluids and tissue. This extra layer of material must be thin enough to avoid unnecessarily thickening the profile of the stent or implantable device, yet must also be thick enough to resist damage during manufacturing, routine handling and implantation of the medical device.

Another disadvantage with current radiopaque marker technology is that, when viewed under fluoroscopic illumination, the radiopaque markers may provide poor or no indication of whether the stent is fully extended. Another significant shortcoming associated with current methods of attaching a radioisotope, radiopaque marker material or drug onto a stent is that these methods can be tedious, imprecise, and require the performance of many sequential processing steps, which greatly increase the stent manufacturing cost.

SUMMARY OF THE INVENTION

The invention provides for improved designs of implantable medical devices such as stents and methods for manufacturing same. The implantable medical devices and stents are manufactured from tubular blanks that are formed by inserting a tightly fitting inner tubular member into an outer tubular member. The inner tubular member may include cavities or microdepots formed on the outer surface of the inner tubular member. The cavities or microdepots may be filled with radioactive, radiopaque and/or therapeutic substances. Channels may also be formed on the outer surface of the inner tubular member to connect the cavities or microdepots with a body lumen. The invention also provides methods describing the application of materials to be deposited in or on the microdepots to render the stent or other implantable medical device radioactive, radiopaque, or therapeutic, either in whole or in part. Rendering the implantable medical device radiopaque allows the use of fluoroscopy to assist in placing the implantable medical device or stent at a desired location in the lumen of a vessel or duct.

In one embodiment, the stent or implantable medical device has a plurality of undulating cylindrical elements or rings that are interconnected by connecting elements. The stent or implantable medical device is manufactured by laser cutting a stent pattern from a tubular blank that is formed by tightly inserting an inner tubular member into an outer tubular member. Thus, the resulting stent structure cut from the tubular blank is a composite of the inner and outer tubular members.

In another embodiment, cavities or microdepots may be formed on the outer surface of the inner tubular member by an etching or machining process. The microdepots may be formed over the entire surface of the stent or medical device, or they may be formed in only selected areas of the device, such as in areas adjacent the distal and proximal ends of the device. This embodiment is advantageous in that the microdepots may be distributed on the outer surface of the inner tubular member in such a way that the distribution, or pattern, of the microdepots coincides with the pattern of the stent or implantable medical device structure formed of cylindrical elements and connecting elements. In this manner, the microdepots are contained within the overall wall thickness of the structure of the stent or implantable medical device.

The inclusion of cavities or microdepots on the outer surface of the inner tubular member provides a carrier for materials, such as radioisotopes, radiopaque materials, or therapeutic chemicals or drugs to deposited on the inner tubular member. Radiopaque materials to be deposited on the inner tubular member include materials known in the art of radiopaque markers, such as silver, gold, platinum or tantalum, or other materials that are compatible with implantation in a body lumen or duct and which are visible under fluoroscopy or other body vessel/organ imaging system. Radioactive materials that may be deposited in the cavities or microdepots on the outer surface of the inner tubular member include beta-emitting radioisotopes and gamma-emitting radioisotopes. Therapeutic substances, such as chemicals and drugs may also be deposited in the cavities or microdepots.

The microdepots may be formed over the entire surface of the stent or implantable medical device, or they may be formed in only selected areas of the device, such as in areas adjacent the distal and proximal ends of the device. Even if microdepots are formed over the entire outer surface of the device, the materials to be deposited may be applied to only selected microdepots. For example, radiopaque material may be deposited only in microdepots adjacent the distal and proximal ends of the device. Deposition of radioactive and radiopaque material in microdepots located on the outer surface of the inner tubular member is advantageous in that the radioactive and radiopaque materials are not exposed to the blood or ductal fluid stream flowing through the interior of the stent or implantable medical device. This helps prevent any deleterious effect on the blood or ductal fluid caused by the radioactive and radiopaque material.

In another embodiment, channels may be provided on the outer surface of the inner tubular member extending from the cavities or microdepots to areas of the inner tubular member that will be cut away during processing of the tubular blank. In this manner, pathways between the microdepots and the body or duct lumen in which the stent or implantable medical device is implanted may be provided. These pathways may be sized so as to control the release rate of therapeutic substances deposited in the cavities or microdepots to the lumen.

In one embodiment of a method to manufacture stents or implantable devices in accordance with the invention, an inner tubular member is provided that may include cavities or microdepots formed on its surface. Materials, such as radioisotopes, radiopaque materials or therapeutic substances may be deposited in the cavities or microdepots. In one variation, where the stent or implantable device is intended to deliver a therapeutic substance, channels are cut into the outer surface of the inner tubular member to provide a pathway between the cavities or microdepots and a body lumen to allow for controlled delivery of the therapeutic substance to the body lumen. The completed inner tubular member is inserted into the outer tubular member such that the inner and outer tubular members are in tight fitting engagement. The tubular blank is then mounted in a collet, and the blank may be indexed so that the pattern of microdepots formed on the inner tubular member coincides with a stent or implantable device pattern that is cut into the tubular blank using a suitable computer controlled laser. The laser cutting machinery includes the capability of moving the laser and mounted tubular blank in a programmed manner to cut a desired structural pattern in to the blank. In another variation, the cutting speed and relative movement of the laser and blank are adjusted so that, while heating of the blank by the laser is minimized, local heating at the beam site is allowed to occur and results in thermal bonding of the outer and inner tubular members.

In another embodiment, materials to be deposited in the microdepots are deposited in the microdepots on the outer surface of the inner tubular member by dipping or immersing the inner tubular member into a mixture or solution of material atoms and a suitable solvent or suspension agent. Such a solution or mixture may include, for example, phosphoric acid, Freon or other solvent. In another approach, the material atoms may be suspended in a polymer solution having material characteristics, such as viscosity or wetting properties, that suspends the material atoms in the polymer solution while coating the atoms with the polymer.

The material atoms may be applied to the surface of the inner tubular member using a variety of methods, such as dipping or immersion. The entire inner tubular member may be dipped or immersed either in whole, or in part. For example, only the areas of the inner tubular member adjacent to areas that will become the distal and proximal ends of the stent or implantable medical device when manufacturing is completed may be dipped or immersed in the mixture or solution containing the material atoms.

Alternatively, the mixture or solution containing the material atoms to be deposited may be deposited in the cavities or microdepots of the inner tubular member using microinjection. In this method, the mixture or solution containing the material atoms is injected into the cavities or microdepots covering the outer surface of the inner tubular member, or the atoms may be injected into cavities or microdepots in selected areas of the inner tubular member.

When the material solution or mixture has coated the inner tubular member, excess material solution or mixture may be removed from the inner tubular member by centrifuging or shaking the inner tubular member. Centrifuging is particularly advantageous, since the centrifugal force assists distribution of the solution across the microdepots and the solution stripped from the inner tubular member may be recycled and reused, thus minimizing loss of material and reducing cost.

In another embodiment of the present invention, the coated inner tubular member may be heated to remove excess solvent or solution and to bind radiopaque material atoms on the surface of the inner tubular member. The heating process may be accomplished using various methods of applying heat in a controlled manner to the inner tubular member, such as using a thermal oven, an inert gas plasma, exposing the coated inner tubular member to an electric arc, or by subjecting the radiopaque atoms coating the inner tubular member to low power exposure from an excimer laser.

In yet another embodiment of the present invention, the material atoms to be deposited may be deposited on the surface of the inner tubular member using an electrodeposition process. In this embodiment, the inner tubular member is attached to a cathode or negative terminal of an electrical current source and dipped or immersed into a positively charged ion mixture or solution of atoms of the material to be deposited. When current flow is initiated, the ions are attracted to the cathode and coat the surface of the inner tubular member.

Other features and advantages of the present invention will become more apparent from the following detailed description, taken in conjunction with the accompanying drawings, which illustrate, by way of example, the principles of the invention.

BRIEF DESCRIPTION OF THE DRAWINGS

FIG. 6 is a flow chart illustrating the major steps of one embodiment of the method of this invention.

FIG. 7 is a flow chart illustrating the major steps of another embodiment of the method of this invention.

DETAILED DESCRIPTION OF THE PREFERRED EMBODIMENTS

The present invention provides a stent or intraductal implant device having radiopaque material, radioisotopes or therapeutic chemicals or drugs deposited or affixed to the body of the stent. Also provided is a method for simultaneously depositing and affixing radiopacifiers, radioisotopes and/or drugs onto such stents or intraductal implant devices.

In the following detailed description, numerous specific details are set forth in order to provide a more thorough understanding of the present invention. However, it will be apparent to those skilled in the art to which this invention pertains that the present invention may be practiced without these specific details. In other instances, well-known devices, methods, procedures, and individual components have not been described in detail so as not to obscure aspects of the present invention.

Figure 1:
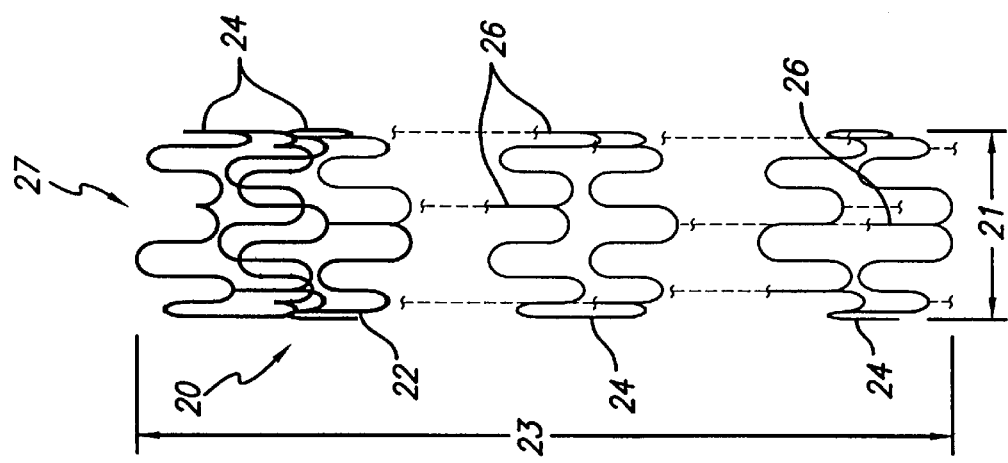
FIG. 1 is a perspective view of a stent embodying the present invention in an unexpanded state.

FIG. 1 is an enlarged perspective view of one embodiment of an implantable medical device, such as a stent 20, practicing the invention. Generally, stent 20 is a thin-walled cylindrically shaped structure having an expanded or extended diameter 21, an outer surface 22, and a longitudinal length 23. In this embodiment, stent 20 has a radially expandable cylindrical mesh having a plurality of undulating cylindrical elements or rings 24 which are interconnected with one or more connecting elements or links 26 such that the undulating cylindrical elements are generally aligned on a common longitudinal axis 27. Various configurations for the placement of the interconnecting elements are possible, and the number of undulations of the cylindrical elements or rings may also be varied to accommodate placement of connecting elements 26.

Figure 2:
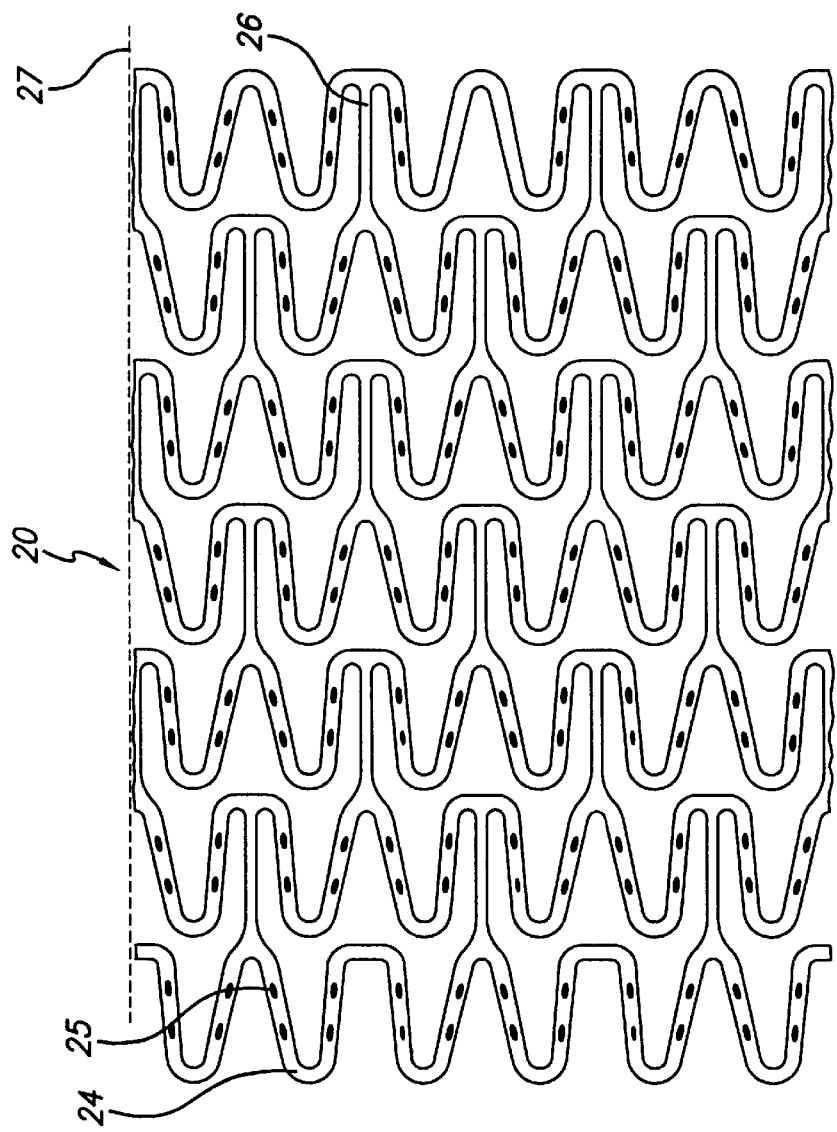
FIG. 2 shows a flat two-dimensional section detail of the stent of FIG. 1 illustrating the undulating pattern of the stent and location of microdepots on the undulating elements.

FIG. 2 illustrates a detailed two-dimensional view of the flexible stent 20 of FIG. 1 at 2—2. Also shown are cavities, or microdepots 25 located on the undulations of the cylindrical elements or rings 24. The cavities or microdepots 25 disposed on the stent may have a frustum (truncated cone) configuration with a low open surface to pore volume ratio. Microdepots 25 may include various other geometries depending on the type of material, such as, for example, a radioisotope, anti-platelet drug, or radiopacificer material, to be deposited on the stent, the type of medical application the stent will be used for, and the stent manufacturing preferences. While the connecting elements 26 of FIG. 2 are shown without cavities or microdepots 25, such may also be formed on the outer surface of the connecting elements if desired.

The afore-mentioned stent 20 and similar stent structures can be made in many ways. However, the preferred method of making the stent is to cut a thin-walled tubular member, such as stainless steel tubing, to remove portions of the tubing in the desired pattern for the stent, leaving relatively untouched the portions of the metallic tubing which are to form the stent. One method of cutting the steel tubing into the desired pattern for the stent is by means of a machine-controlled laser as illustrated schematically in FIG. 3.

The stent 20 is desired to be implantable and may be made of any material known in the field of stent procedure therapy including metal or metal alloys such as titanium, 316L stainless steel, and nitinol. Alternatively, a non-metal material such as polymer-type, ceramic; or a composition thereof may be used to form the stent. The stent may also be formed from a material or materials resulting in a radioactive stent.

The stent or intraductal medical device diameter is typically very small, depending on the diameter of the vessel or duct in which the stent or intraductal medical device is to be implanted. Accordingly, the tubing from which the stent or intraductal medical device is made must necessarily also have a small diameter. Typically, a stent to be used in coronary arteries has an outer diameter on the order of about 0.06 inch in the unexpanded condition, the same outer diameter of the tubing from which it is made, and can be expanded to an outer diameter of 0.1 inch or more. The typical wall thickness of the tubing is about 0.003 inch, but may be in the range of 0.002 to 0.004 inch.

Figure 3:
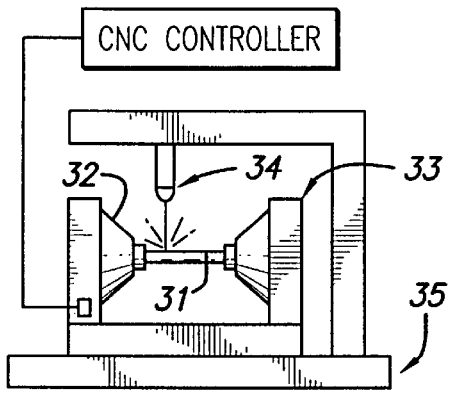
FIG. 3 is a schematic representation of equipment for selectively cutting the tubing in the manufacture of a stent.

Referring to FIG. 3, the tubing 31 is put in a rotatable collet fixture 32 of a machine-controlled apparatus 33 for positioning the tubing 31 relative to a laser 34. According to machine-encoded instructions, the tubing 31 is rotated and moved longitudinally relative to the laser 34 which is also machine controlled. The laser selectively removes the material from the tubing by ablation and a pattern is cut into the tube. The tube is therefore cut into the discrete pattern of the finished stent.

The process of cutting a pattern for the stent into the tubing is automated except for the loading and unloading the length of tubing. This loading may be done, for example, using a CNC-opposing collet fixture 32 for axial rotation of the length of tubing, in conjunction with a CNC X/Y table 35 to move the length of tubing axially relatively to a machine-controlled laser as described. The entire space between collets can be patterned using the laser set-up of the foregoing example. The program for control of the apparatus is dependent on the particular configuration used and the pattern to be ablated in the tubing. The laser used may be a $CO_2$ laser, or it may be a Q-switched Nd/YAG laser, such as is available from Quantronix of Hauppauge, N.Y. The Q-switched Nd/YAG laser may be frequency doubled to produce a green beam at 532 nanometers that allows the laser beam to focused to a spot size small enough to ablate the material of the tubing into the desired pattern. In a typical example, frequency doubling the beam from 1.06 microns to 0.532 microns allows the beam to focused to a spot size that is 2 times smaller, and increases the power density of the beam by a factor of 4 times, making it possible to make smooth, narrow cuts in the tubing in very fine geometries without damaging the narrow undulating cylindrical elements or connecting elements that make up the stent structure. It is contemplated that other lasers may be suitable for the afore-described ablation process, provided that they can provide the necessary spot size and power and can be controlled to ablate a pattern having the fine geometry of a desired stent pattern.

Alternatively, the stent pattern may be cut from the tubing using an electro-etching process. In this process, which is well known in the art, a layer of chemically resistant material is deposited on the surface of the tubing such that the layer of resistant material forms the desired stent pattern on the outer surface of the tubing. The tubing with the resistant layer may then be exposed to a chemical etching process where the unwanted metal of the tube that is not protected by the resistant layer is etched away, leaving the stent pattern behind. The resistant layer may then be removed from the remaining metal of the stent using processes well known in the art.

Depending on the type of use, the length 23 of the stent 20 (FIG. 1) may be in the range of approximately 5 to 100 +mm for vascular stents. For stents used in procedures to inhibit the proliferation of tumor neoplasma in ductal organs, the length 23 of the stent may be in the range of approximately 5 mm to 30 cm.

When deployed in their extended or expanded configuration, vascular stents typically have an expanded diameter 21 in the range of approximately 2 to 12 mm. For stents used in procedures to inhibit the proliferation of tumor neoplasma in ductal organs, the expanded diameter 21 of the stent 20 is generally in the range of approximately 2 mm to 4 cm.

It should be noted that although this invention is described using a stent as an example of an implantable device, this invention is not limited only to stents or stent-like devices. This invention can be practiced using other implantable medical devices, such as, for example, implantable grafts.

Figure 4:
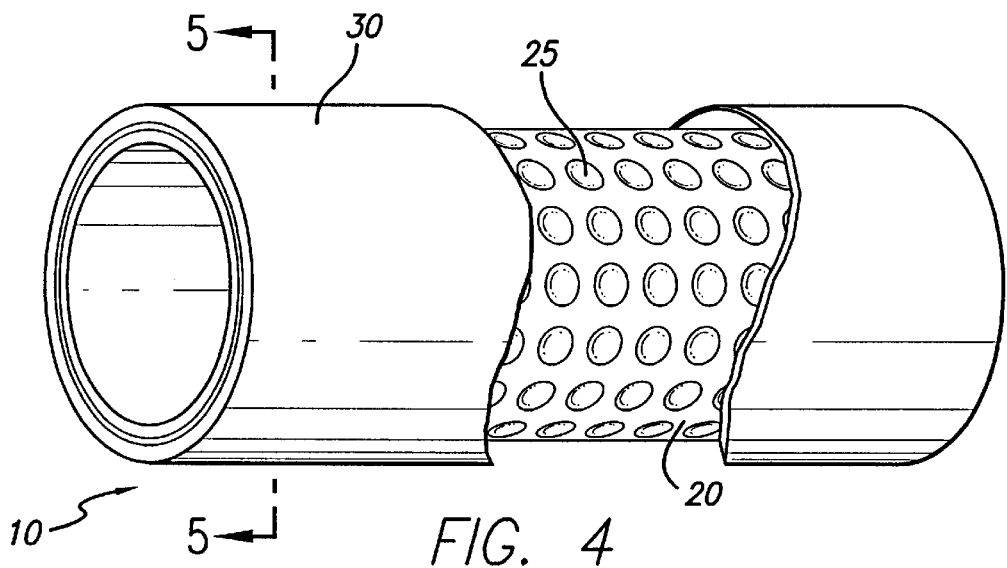
FIG. 4. is a perspective view of a tubular blank from which the stent of FIG. 1 may be formed showing an inner tube including microdepots and channels inserted into an outer tube.
Figure 5:
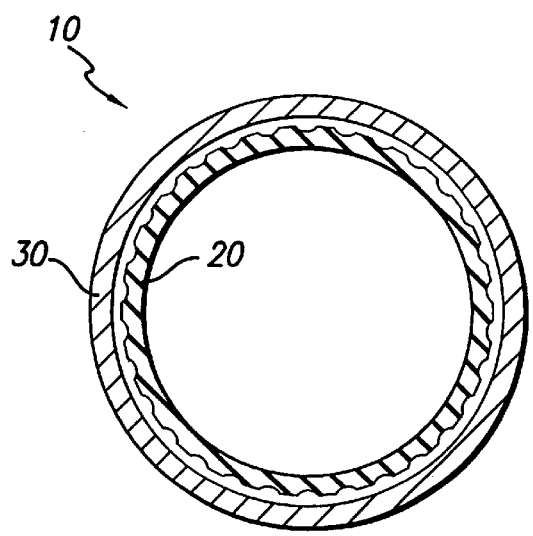
FIG. 5 is a cross-sectional view of the invention of FIG. 1 illustrating the close fitting engagement of the inner and outer tubes.

Referring now to FIG. 4, an embodiment of the present invention utilizing a tube-within-a-tube approach for providing a stent or intraductal medical device having cavities or microdepots which may be loaded with radiopaque marker material, radioisotopes or therapeutic chemicals or drugs is described. Instead of machining a tube blank that is formed from a single piece of tubing material, a blank 40 is prepared which has an outer tube 42 enclosing an inner tube 44. The diameter of outer tube 42 will be the same size as the outer diameter of the unexpanded stent or intraductal medical device to be cut from the blank. The outer diameter of inner tube 44 is sized such that inner tube 44 fits tightly within the lumen of outer tube 42. This arrangement is best shown in FIG. 5.

The blank 40 will typically have an overall wall thickness in the range of 0.002 to 0.004 inch, and usually about 0.003 inch. Thus, the wall thicknesses of both the outer tube 42 and the inner tube 44 contribute to the overall wall thickness of blank 40. Generally, the wall thickness of the outer tube 42 will be thinner, that is, less than the wall thickness of inner tube 44, although the wall thicknesses of both tubes may be the same. One embodiment of the present invention may be formed where the wall thickness of inner tube 44 is about 70–80 percent of the overall wall thickness of blank 40. Thus, the wall thickness of outer tube 42 would be 20–30 percent of the overall wall thickness of the blank 40 in this embodiment.

Forming blank 40 in this manner is particularly advantageous where microdepots are to be included on the stent or intraductal medical device. For example, microdepots 45 may be formed on the outer surface of inner tube 44 before it is inserted into outer tube 42. Additionally, microdepots 45 may be loaded with radiopaque material, radioisotopes and/or therapeutic chemicals or drugs prior to insertion into outer tube 42. In this way, the radiopaque material, radioisotopes and/or therapeutic chemicals or drugs may be covered by the inner wall of outer tube 42 and contained within the overall wall thickness of the stent. This arrangement is advantageous in that contact between body fluids flowing within the lumen of the stent or intraductal medical device and tissue surrounding the stent and the radiopaque material, radioisotopes and/or therapeutic chemicals or drugs is prevented.

The microdepots 45 may be formed on the outer surface of inner tube 44 by chemical etching, laser ablation, or other suitable methods known in the art. The distribution of microdepots 45 on the outer surface of inner tube 44 may be configured to coincide with the pattern of cylindrical elements or rings or connecting elements of the stent or device pattern. In this manner, when the stent pattern is cut from blank 40, the remaining metal forming the structure of the stent will include microdepots 45 contained within the wall thickness of the stent stent structure. Moreover, the distribution of microdepots 45 may be configured such that the microdepots are evenly distributed over the entire structure of the stent or intraductal medical device, or, alternatively, the microdepots may be arranged on the outer surface of inner tube 44 only in the areas of inner tube 44 that will become the areas adjacent to the distal and proximal ends of the completed stent.

A method of manufacturing a stent or intraductal medical device incorporating the present invention will now be described. Tubing to be used to form inner tube 44 is selected from materials suitable for implantation in the body, such as 316L stainless steel, and may be cut to a desired length for further processing. The outer surface of inner tube 44 may be etched or machined to form a plurality of cavities, or microdepots 45 on the outer surface of inner tube 44. The microdepots 45 on the outer surface of inner tube 44 may be distributed so that the microdepots coincide with the structure of the stent or device to be made.

Alternatively, where a therapeutic chemical or drug is to be loaded into the microdepots 45, a pattern of channels 48 may be etched or machined into the outer surface of inner tube 44 connecting the microdepots 45 with the edges of the stent structure when the stent is completed. In this way, pathways from the microdepots 45 incorporated into the structure of the stent when inner tube 44 is inserted into outer tube 42 may be obtained that connect the microdepots to the lumen of a vessel or duct when the stent is implanted. These pathways allow the flow of therapeutic chemical or drug from the microdepot buried within the wall thickness of the stent structure to the outer surface of the stent structure. The width and depth of the channels formed on the outer surface of inner tube 44 will depend on the material characteristics of the therapeutic chemical or drug to be delivered and the desired rate of drug delivery to the body, and may be adjusted accordingly. As described previously, in one embodiment, the microdepots and channels may be etched or machined into the outer surface of inner tube 44 using chemical etching techniques well known in the art, or by a laser controlled by a software program similar to that previously described with reference to cutting a stent pattern from a tube. Alternatively, the pattern of microdepots and stent structure may be intentionally misaligned so that some microdepots are formed overlapping what will become the edge of the final stent structure, thus exposing at least a portion of the microdepot to the lumen of the vessel or duct. Such a construction allows for a relatively controlled seepage of therapeutic chemical or drug from the microdepot to the vessel or duct lumen.

After the microdepots 45 or channels are formed on the outer surface of inner tube 44, the microdepots may be loaded with radiopaque materials, radioisotopes or therapeutic chemicals or drugs. In general, radiopaque materials, radioisotopes or therapeutic chemicals or drugs may be deposited in the microdepots by a variety of methods. These materials may be deposited individually or in combination, either simultaneously or sequentially. Various embodiments of methods for loading such materials are described in more detail below.

When the loading process is completed, inner tube 44 is inserted into outer tube 42. The pattern of microdepots is indexed so that when blank 40 is inserted in a CNC-collet fixture 32 (FIG. 3), blank 40 may be oriented so that when the stent pattern is cut into the stent, the stent structure formed by the cutting operation coincides with the pattern of microdepots formed on the outer surface of inner tube 44. Such indexing is well within the scope of techniques known to those skilled in the art of precision computer controlled machining.

Referring again to FIG. 3, blank 40 is put in a rotatable collet fixture 32 of a machine-controlled apparatus 33 for positioning the blank 40 relative to a laser 34. According to machine-encoded instructions, the blank 40 is rotated and moved longitudinally relative to the laser 34 which is also machine controlled. The laser selectively removes the material from blank 40 by ablation and a pattern is cut into the tube. The tube is therefore cut into the discrete pattern of the finished stent.

As described above, excess material is removed from blank 40 by ablation by laser 34. During this ablation, blank 40 is heated by laser 34 in the area being ablated. The laser power level, spot size and speed of relative motion between laser 34 and blank 40 are controlled to minimize heat build up in blank 40 during the cutting process. However, the cutting speed may also be controlled so that while overall heating of blank 40 is minimized, some localized heating of blank 40 in the area of the laser beam is allowed to cause thermal bonding between the inner wall of outer tube 42 and the outer wall of inner tube 44. In this manner, the stent structure incorporating material remaining from inner tube 44 and outer tube 42 after cutting will be prevented from separating during further processing or use of the stent. This thermal bond is also advantageous where therapeutic chemicals or drugs have been loaded into the microdepots, ensuring that chemical or drugs flow only through designated channels or pathways, thus controlling the rate of delivery of the chemical or drug.

FIG. 6 is a flow chart illustrating the major steps of one embodiment of the method of the present invention wherein radioisotope atoms and radiopaque atoms may be deposited simultaneously in the microdepots. While the following methods are described in terms of simultaneous deposition of radioisotope atoms and radiopaque atoms in microdepots 45 formed on the outer surface of inner tube 44 (FIG. 4), it will be understood by those skilled in the art that this deposition does not need to be done simultaneously, but may be accomplished sequentially. The methods described herein are also useful where it is desired to deposit only radioisotope atoms or radiopaque atoms, but not both, in the microdepots 45 on the outer surface of inner tube 44.

In this embodiment, the method begins by simultaneously depositing, or loading, radioisotope atoms and radiopaque atoms onto an inner tube 44 to be incorporated into an implantable medical device such as a stent or intraductal medical device in step 310. The deposition of radioisotope atoms and radiopaque atoms on inner tube 44 is generally achieved by depositing the atoms as part of a mixture or solution using a number of processes such as dip-coating, which may be followed by a centrifugation or a shaking action, electrodeposition, sputtering, micro-injection, thin-film spray coating, ion beam assisted deposition (IBAD), or a combination thereof.

Low-intensity implantable radioactive stents manufactured using an embodiment of the present invention generally employ beta-emitting or low energy gamma-emitting radioisotopes. A beta-emitter radioisotope, such as phosphorus-32 ($P^{32}$), which emits low-energy, short half-life beta particles, is typically desired to provide optimum therapeutic treatment with maximum patient safety. The list of possible beta emitting and low-penetration gamma-emitting radioisotopes includes, but is not limited to, $Sn^{123}$, $Sr^{89}$, $P^{33}$, $Pd^{103}$, and $I^{125}$. Other types of treatments, such as treatment to inhibit proliferation of tumor neoplasma in ductal organs, such as the kidney, pancreas, liver and esophagus, may require a more penetrating gamma-emitting radioisotope such as $Ir^{192}$, $Co^{57}$, $Rh^{106}$ and $Tc^{99}$.

The radiopaque marker materials to be deposited on the stent may include any materials known in the art of radiopaque markers, such as silver, gold, platinum, or tantalum, that allow markers to become visible under fluoroscopy or other body vessel/organ imaging system.

Referring again to FIG. 6, in one embodiment, the radioisotope atoms and radiopaque atoms, following deposition onto the microdepots 45 of inner tube 44, undergo a heating process that causes the radiopaque atoms to adhere to the surface of the microdepots 45, as illustrated by step 320. During step 320, the radiopaque atoms are heated to a temperature high enough so that they soften and adhere, or bond, to the surface of the microdepot 45 on the inner tube 44. During the heating process, the temperature of the radiopaque metal atoms is raised to a temperature that is in the range of approximately 200 to 900 degrees Celsius. The radiopaque metal atoms are maintained at this temperature for a time period that is in the range of approximately 1 minute to 3 hours. The heating process may be performed using any techniques and devices known in the art, including, for example, thermal processing, inert gas plasma processing, electric arc processing, an excimer laser exposure at low power, or any laser that uses a noble-gas halide to generate radiation usually in the ultraviolet region of the spectrum.

Referring now to FIG. 7, in another embodiment of the present invention, radioisotope atoms and radiopaque atoms may be deposited or loaded into the microdepots 45 on the outer surface of inner tube 44. In this embodiment, deposition of the radioisotope atoms and radiopaque atoms begins at step 410 by preparing a mixture or solution of radioisotope atoms and radiopaque material atoms. In one variation of this embodiment, radioisotope atoms and radiopaque metal atoms such as gold (Au) are suspended or dissolved in an aqueous solution of phosphoric acid $H_3P^{32}O_4$. Alternatively, at step 410, if a radioisotope other than phosphorous-32 is desired, the radiopaque atoms and other radioisotopes such as iridium, indium, or other such gamma-emitting or beta-emitting isotopes can be suspended in a highly wetting solvent such as Freon™, THF (Tetra Hydrofuran), or the like. Other suitable solvents include toluene, cyclohexanone, dimethly acetamide (DMAc) and Methoxopropanol acetate (PM acetate).

In another approach, the radioisotope atoms and radiopaque metal atoms may be suspended in a polymer solution. The material characteristics of the polymer solution, such as, for example, the viscosity of the polymer solution, enables the radioisotope atoms and radiopaque atoms to become coated with the polymer. Examples of suitable polymers include polybutlymethacrylate (PBMA), polymethlymethacrylate (PMMA), polyethylene glycol-5000 (PEG-5000) and ethylene vinyl alcohol (EVAL).

At step 420, the mixture of radioisotope atoms and radiopaque material atoms is applied or deposited onto the microdepots 45 of inner tube 44. In one approach, the mixture is applied onto the microdepots by immersing inner tube 44 in the aqueous solution of phosphorous acid $H_2P^{22}O_4$ containing the radioisotope atoms and radiopaque metal atoms by dipping inner tube 44 into the solution. Inner tube 44 is immersed in the aqueous solution of phosphorous acid $H_3P^{32}O_4$ for a time period that is in the range of approximately 1 second to 5 minutes. During this immersion or dipping, the radioisotope atoms and radiopaque metal atoms coat the structure of inner tube 44.

Alternatively, at step 420, radioisotope atoms and radiopaque atoms may be suspended in a highly wetting solvent such as Freon™, THF (Tetra Hydrofuran), or the like. In one alternative embodiment, the mixture of radioisotope atoms and radiopaque material atoms, which may also contain a polymer, is applied onto inner tube 44 by dipping or immersing the stent into the Freon or solvent solution for a time period that is in the range of approximately 1 second to 5 minutes such that the radioisotope atoms and radiopaque metal atoms are deposited onto the structure of inner tube 44 by capillary action.

In one embodiment, radioisotope atoms and radiopaque atoms are mixed into a solution containing about thirty-five percent (35%) cyclohexanone and about sixty-three percent (63%) dimethyl acetamide by weight. Thus, the radioisotope atoms and radiopaque atoms comprise about two percent (2%) by weight of the mixture or solution. Alternatively, the concentration of radioisotope atoms and radiopaque atoms in the mixture or solution may be in the range of one to fifty percent (1%–50%) by weight, with the concentrations of the solvent and/or polymer adjusted accordingly to provide a mixture or solution having properties suitable for application of the mixture or solution to the stent or medical device. The ratio of radioisotope atoms to radiopaque atoms may be adjusted according to the level of radioactivity and radiopacity desired in the finished device.

At step 430, the coated or loaded inner tube 44 is removed from the mixture or solution and is then subjected to vigorous and/or rapid movement. This rapid movement of inner tube 44 acts to remove any excess mixture or solution containing the radioisotope atoms and radiopaque material atoms from the surface of inner tube 44 and/or from cavities or microdepots 45. Typically, little of the mixture or solution will remain on the surface of inner tube 45, but will remain in the cavities or microdepots.

In one embodiment, step 430 is performed by subjecting the coated inner tube 44 to centrifugation action. In this embodiment, inner tube 44 is mounted onto a mandrel and is spun at a rotational speed in the range of approximately 3000 to 7000 rotations per minute (rpm) for a time period that is in the range of approximately 1 to 3 minutes. When the centrifugation step 430 may be adjusted by increasing or decreasing the rotational speed of the mandrel such that the radioisotope atoms and radiopaque material deposited in the microdepots achieves a desired thickness.

One advantage of suspending the radioisotope atoms and radiopaque material atoms in a mixture or solution containing a polymer to deposit the radioisotope atoms and radiopaque material atoms in the microdepots 45 is that the centrifugation step 430 generally removes most or all the mixture or solution of radiopaque metal atoms present in areas of inner tube 44 other then the microdepots 45. This result is due in part because the radioisotope atoms and radiopaque metal atoms inside the microdepots are embedded in the viscous polymer material within the volume of the microdepot, and are thus removed at a slower rate than the atoms coating the outer surface of inner tube 44. Thus, the polymer present in the mixture or solution acts as a binder for the atoms deposited within the microdepot.

In another embodiment of the method employing step 430, the removal of excess radioisotope atoms and radiopaque metal atoms solution or mixture from the surface of inner tube 44 is achieved by subjecting inner tube 44 to a shaking-like motion.

It should be noted that the processing times for keeping inner tube 44 immersed into the solution containing the radioisotope atoms and radiopaque atoms, $t_{dipping\ tube}$, or for rapidly moving or shaking inner tube 44, $t_{shaking\ tube}$, or centrifuging (i.e., spinning) inner tube 44 in the centrifugation chamber, $t_{centrifuge\ tube}$, may vary considerably from the times provided in the above exemplary embodiment. These processing times may be modified to take into consideration the type or design of the inner tube used and the number and distribution of microdepots formed on the surface of the inner tube. Moreover, the type of aqueous solution or mixture used to apply the radioisotope atoms and radiopaque material may also alter the immersion and/or shaking or spinning times.

Referring again to FIG. 7, following the deposition of the radioisotope atoms and radiopaque mixture/solution onto the microdepots and removal of excess solution from inner tube 44, inner tube 44 may be thermally post-processed to allow the radiopaque metal atoms to adhere to the stent.

It will be understood by those skilled in the art that such thermal postprocessing will only be required by certain mixtures and solutions to promote adherence of the radiopaque atoms to the surface of inner tube 44. Depending on the solutions used, post processing may not be required. In one embodiment, as part of step 440, the radiopaque metal atoms may be heated to a point such that they soften and form a coherent mass that is masked inside microdepots 45. During this process, the temperature of the radiopaque metal atoms is raised to a temperature that is in the range of approximately 200 to 900 degrees Celsius. The radiopaque metal atoms are maintained at this temperature for a time period that is in the range of approximately 1 minute to 3 hours.

The thermal post-processing step 440 may be performed using any techniques and devices known in the art of metal processing. The choice of the heating process technique used depends on a number of variables such as the type of process employed to deposit the radioisotope atoms and radiopaque atoms on inner tube 44 (i.e., dip-coating plus centrifugation, electroplating, ion implantation, spay coating), manufacturing preferences such as ease, cost and complexity and other variables.

In one embodiment, heating process step 440 may be accomplished using a thermal processing approach. In another embodiment, heating process step 440 may be accomplished using an inert gas plasma processing approach where the power for the plasma cycle is modified to allow the opaque material atoms such as gold to soften and stabilize themselves within the microdepots 25. In yet another embodiment, heating process step 440 may be achieved by subjecting the radiopaque atoms to low power exposure from an excimer laser which typically uses a noble-gas halide to generate radiation usually in the ultraviolet region of the spectrum. In yet another embodiment, heating process step 440 may be accomplished by subjecting the radiopaque metal atoms to heat from an electric arc.

It should be noted that step 440 is not required to practice the invention. For example, where the radioisotope atoms and radiopaque metal atoms are in a polymer-like solution that is used to coat the microdepots or cavities on the outer surface of inner tube 44, the excess solution may be removed from inner tube 44 and the inner tube allowed to air-dry for a specific period of time. As the solvent or like material dries out, the radioisotope atoms and radiopaque atoms remain embedded in the polymer inside the volume of the microdepots.

Depositing or loading radioisotope atoms and radiopaque metal atoms onto a microdepot-patterned inner tube 44 and using centrifugation to remove excess solution has a number of advantages. The centrifugal force helps redistribute the solution fluid flow across the surface of inner tube 44. The method may be performed using a semi-automated manufacturing mode, thus reducing manufacturing times and costs. Minimal handling of the radioactive solution in a closed system assures minimum exposure to the operator. The radioisotope and radiopaque solution that strips off inner tube 44 can be recycled and reused, thus minimizing loss of material and reducing cost.

Figure 8:
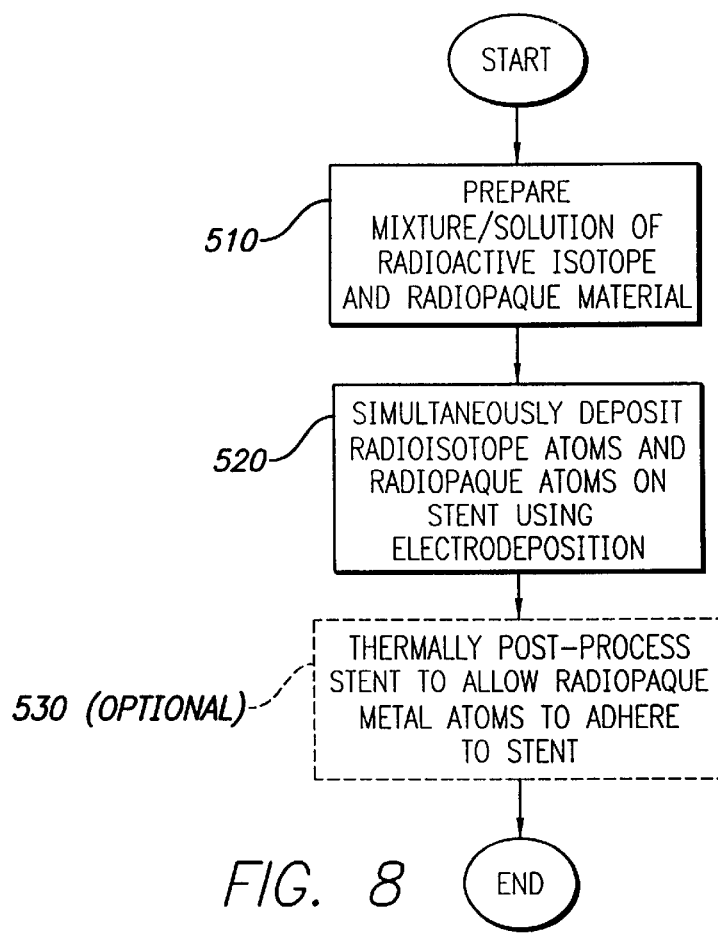
FIG. 8 is a flow chart illustrating the major steps of yet another embodiment of the method of this invention.

Referring now to FIG. 8, in another embodiment of the method of this invention, radioisotope atoms and radiopaque atoms are deposited or loaded onto the inner tube 44 using an electrodeposition process. As part of the electrodeposition process, radioisotope atoms will be co-deposited with radiopaque atoms of metal such as gold (Au) are deposited by electrochemical deposition of Au through faradic current flux.

The method of this embodiment begins at step 510 by preparing a positively charged ion mixture or solution of radioisotope atoms and radiopaque material atoms. In one approach, radiopaque metal atoms, such as gold (Au), are suspended or dissolved in an aqueous solution of phosphoric acid $H_3P^{32}O_4$. Alternatively, at step 510, if a radioisotope other than phosphorous-32 is desired, the radiopaque atoms and other radioisotopes such as iridium, indium, or other such gamma-emitting or beta-emitting isotopes can be suspended in a highly wetting solvent such as Freon™, THF (Tetra Hydrofuran), or the like.

Inner tube 44 is connected to the cathode or negative terminal of an electrical current source at step 520 while the anode or positive electric terminal of a source is connected to a mandrel or similar device that is dipped into the positively charged ion solution of radiopaque metal atoms. The ions are attracted to the cathode and the coating is deposited on the surface of the stent. The thickness of the layer of deposited radioisotope atoms and radiopaque metal atoms depends on the amperage of the electric current, the concentration of the radiopaque metal ions, the length of time that the stent is subjected to the faradic current coating cycle, as well as other electroplating process characteristics known in the art. The thickness of the layer of the deposited radioisotope atoms and radiopaque metal atoms also depends on the particular size and geometrical shape of microdepots 45 formed on the surface of inner tube 44. It is generally desired to have the thickness of the layer "masked" or flat within the microdepot.

Referring again to FIG. 8, following the deposition of radioisotope atoms and radiopaque metal atoms using the electrodeposition process, inner tube 44 may be thermally post-processed to allow the radiopaque metal atoms to adhere to the surface of the microdepots as is described in step 530. This heating process 530 is similar to the process discussed above with reference to step 440 of FIG. 7. This step may be followed by the deposition of other materials, such as, for example, sequential administration of a designed-to-coat blood compatible substance or a therapeutic chemical or drug.

In one embodiment, heating process step 530 may be accomplished using a thermal processing approach. In another embodiment, heating process step 530 may be accomplished using an inert gas plasma processing approach where the power for the plasma cycle may be modified to allow the opaque material atoms, such as gold, to soften and stabilize themselves on the surface of inner tube 44 within the microdepots 45. In yet another embodiment, heating process step 530 may be accomplished by subjecting the radiopaque atoms to low power exposure from an excimer laser which typically uses a noble-gas halide to generate radiation usually in the ultraviolet region of the spectrum. In yet another embodiment, heating process step 530 may be accomplished by subjecting the radiopaque metal atoms to heat from an electric arc.

During the heating process, the temperature of the radiopaque metal atoms is raised to a temperature that is in the range of approximately 200 to 900 degrees Celsius. The radiopaque metal atoms are maintained at this temperature for a time period of 1 minute to 3 hours.

As stated previously with reference to step 440 of FIG. 7, step 530 is not required to practice the invention. The inner tube 44 having microdepots or cavities that are coated with a polymer or polymer-like solution containing radioisotope atoms and radiopaque metal atoms may be allowed to air-dry for a specific period of time instead of heating. As the aqueous solution or solvent or like material dries out, the radioisotope atoms and radiopaque atoms remain embedded in the polymer inside the volume of the microdepots. Therefore, heating the radiopaque atoms to cause them to adhere to inner tube 44 as set forth in step 540 may not be necessary in order to obtain a radiopaque stent.

Figure 9:
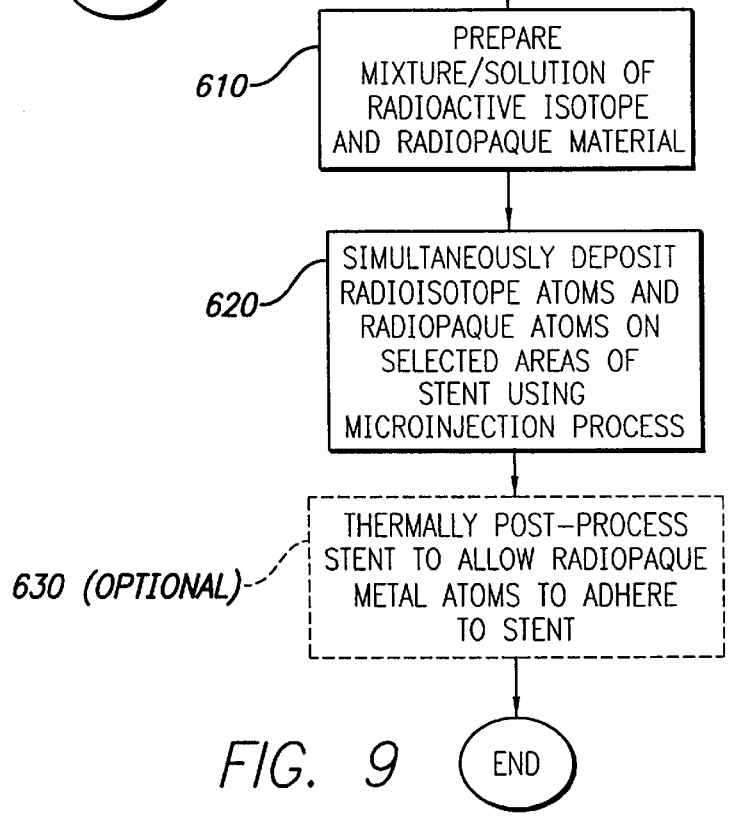
FIG. 9 is a flow chart illustrating the major steps of still further embodiment of the method of this invention.
Figure 3:
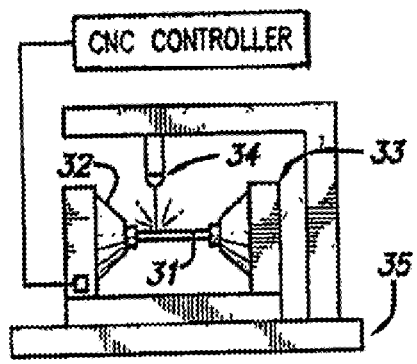
Figure 4:
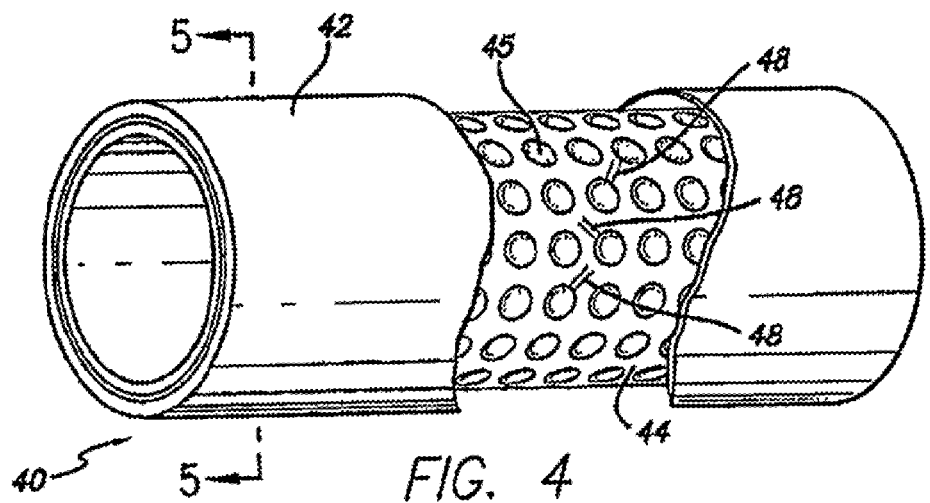
Figure 5:
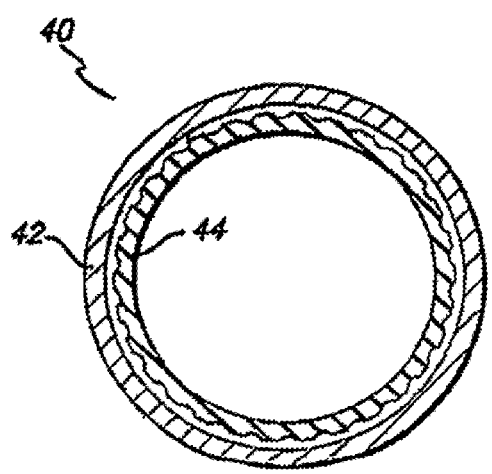

Referring now to FIG. 9, in yet another embodiment of the method of the invention, radioisotope atoms and radiopaque atoms are deposited or loaded inside microdepots 45 using a micro-injection process.

The method of this embodiment begins at step 610 by preparing a mixture or solution of radioisotope atoms and radiopaque material atoms. In one approach, radiopaque metal atoms such as gold (Au) are suspended or dissolved in an aqueous solution of phosphoric acid $H_3P^{32}O_4$. Alternatively, at step 610, if a radioisotope other than phosphorous-32 is desired, the radiopaque atoms and other radioisotopes such as iridium, indium, or other such gamma-emitting or beta-emitting isotopes can be suspended in a highly wetting solvent such as Freon™, THF (Tetra Hydrofuran), or the like.

Inner tube 44 is mounted on a mandrel or similar device and placed in a chamber-like enclosure at step 620. The radioactive and radiopaque solution prepared during step 610 is then injected into microdepots 45 on the outer surface of inner tube 44 using a micro-injector system. The microinjection process may deposit the radioactive and radiopaque solution into all microdepots or only into a specific combination of microdepots such as those positioned adjacent what will become the proximal and distal ends of the completed stent or intraductal medical device. The microinjection process may be performed manually, automatically, or semi-automatically.

Following the radioisotope and radiopaque metal atom deposition using the micro-injection process in step 620, inner tube 44 may be post-processed using a heating or similar technique to allow the radiopaque metal atoms to adhere to inner tube 44 in step 630. The heating process step 630 is similar to the heating process described above with reference to step 440 in FIG. 7.

In one variation of this embodiment, heating process step 630 may be achieved using a thermal processing approach. In another embodiment, heating process step 630 may be accomplished using an inert gas plasma processing approach where the power for the plasma cycle is modified to allow opaque material atoms such as gold to soften and stabilize themselves within microdepots 45. In yet another embodiment, heating process step 630 may be accomplished by subjecting the radiopaque atoms to low power exposure from an excimer laser which uses a noble-gas halide to generate radiation usually in the ultraviolet region of the spectrum. In yet another embodiment, heating process step 630 may be accomplished by subjecting the radiopaque metal atoms to heat from an electric arc.

During the heating process of step 630, the temperature of the radiopaque metal atoms is raised to a temperature that is in the range of approximately 200 to 900 degrees Celsius. The radiopaque metal atoms are maintained at this temperature for a time period of 1 minute to 3 hours.

As discussed previously, it should be noted that step 630 is not required to practice the invention. Inner tube 44 having microdepots or cavities 45 that are coated with a polymer-like solution or mixture containing radioisotope atoms and radiopaque metal atoms may be allowed to air-dry for a specific period of time rather than exposing inner tube 44 and dried solution to heat. As the aqueous solution or solvent or like material dries out, the radioisotope atoms and radiopaque atoms remain embedded in the polymer inside the volume of the microdepots. Therefore, heating the radiopaque atoms to cause them to adhere to the stent as described in step 630 may not be necessary in order to obtain a radiopaque stent.

The radioactive and/or radiopaque stent or implantable medical device manufactured using the methods described herein will be completed with much higher regional radiopacity for the same amount of radiopaque material loading averaged over the total surface area of the stent. One advantage of this method of providing a radiopaque stent is that radiopaque materials can be loaded inside the microdepots and co-processed simultaneously with radioactive isotopes to yield a final stent or implantable medical device that is both radioactive and either radiopaque in its entirety or at selected locations on the stent or device.

The method of this invention is especially well suited for use on implantable medical devices, such as stents or their components, having a microdepot-like pattern disposed on their surface since there is no need to deposit the radiopaque mixture over the entire contour of the device in order to obtain visualization of the entire stent under fluoroscopy. Furthermore, by applying the method of this invention to a stent incorporating an inner tube having microdepots that is tightly inserted into an outer tube, the various negative effects associated with gold coating and the way it interacts with blood cells can be minimized or eliminated, since the microdepots containing the gold radiopaque material are enclosed within the wall thickness of the structure of the stent or intraductal medical device. That is, since the radiopaque material is deposited and affixed only within the volume of the microdepots, that is, positioned within the wall thickness of the structure of the stent, there is very limited or no physical contact between the blood flow in the inner lumen of the stent and the radiopaque material.

While several specific embodiments of the invention have been illustrated and described, it will be apparent that various modifications can be made without departing from the spirit and scope of the invention. Accordingly, it is not intended that the invention be limited, except as by the appended claims.

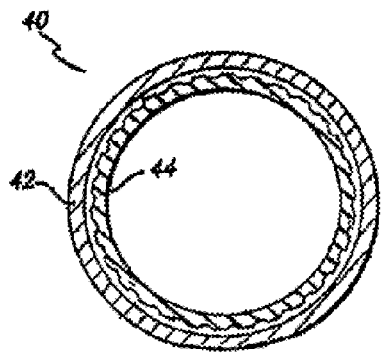

What is claimed:

1. A longitudinally flexible stent for implanting in a body lumen, comprising:
    a plurality of cylindrical elements formed from a tubular member the tubular member including an inner tubular member having a stent pattern formed therein and an outer tubular member having a stent pattern formed therein, the inner and outer tubular members in tight fitting engagement with each other, the cylindrical elements being interconnected so as to be generally aligned on a common longitudinal axis; and
    at least one connecting element for interconnecting the cylindrical elements, the connecting element being formed from the same tubular member as the cylindrical elements, and configured to interconnect the cylindrical elements that are adjacent to each other;
    wherein the stent patterns of the inner tubular member and the outer tubular member are aligned.

2. The stent of claim 1, wherein at least one microdepot is formed on an outer surface of the stent pattern of the inner tubular member.

3. The stent of claim 2, further comprising a radioactive coating affixed on the at least one microdepot.

4. The stent of claim 2, further comprising a radiopaque coating affixed on the at least one microdepot.

5. The stent of claim 2, further comprising a coating including a therapeutic substance affixed on the at last one microdepot.

6. The stent of claim 2, further comprising a radioactive and radiopaque coating affixed on the at least one microdepot in which the coating is formed by simultaneous deposition of a radiopaque material and a radioisotope.

7. The stent of claim 2, further comprising a channel formed in the outer surface of the inner tubular member connecting the at least one microdepot to an opening disposed in an edge of the stent pattern.

8. The stent of claim 7, further comprising a coating including a therapeutic substance affixed on the at least one microdepot.

9. The stent of claim 1, wherein microdepots are formed on an outer surface of the inner tubular member in a microdepot pattern that coincides with the stent pattern of the inner tubular member.

10. A longitudinally flexible stent for implanting in a body lumen comprising:
    a plurality of laser cut cylindrical elements formed from a tubular member, the tubular member including an inner tubular member having a stent pattern and an outer tubular member having a stent patter, the inner and outer tubular members in tight fitting engagement with each other, the cylindrical elements being interconnected so as to be generally aligned on a common longitudinal axis, and the stent patterns of the inner and outer tubular members are aligned;
    at least one connecting element for interconnecting the cylindrical elements, the connecting element being laser cut from the same tubular member as the cylindrical elements, and configured to interconnect the cylindrical elements that are adjacent to each other; and
    at least one microdepot formed on an outer surface of the stent pattern of the inner tubular member.

11. The stent of claim 10, further comprising a channel connecting the at least one microdepot with the body lumen.

12. The stent of claim 10, further comprising a radioactive coating affixed in the at least one microdepot.

13. The stent of claim 10, further comprising a radiopaque coating affixed in the at least one microdepot.

14. The stent of claim 10, further comprising a coating including a therapeutic substance affixed in the at least one microdepot.

15. The stent of claim 10, further comprising a radioactive an radiopaque coating affixed in the at least one microdepot in which the coating is formed by simultaneous deposition of a radiopaque material and a radioisotope.

16. The stent of claim 11, further comprising a coating including a therapeutic substance affixed in the at least one microdepot.

17. A stent comprising:
    a plurality of cylindrical elements formed from a tubular member having an inner tubular member having a stent pattern and an outer tubular member having a stent pattern, the cylindrical elements are interconnected so as to be generally aligned on a common longitudinal axis and the stent patterns of the inner and outer tubular members are aligned;

at least one connecting element formed from the same tubular member as the plurality of cylindrical elements for interconnecting the plurality of cylindrical elements;

a plurality of cavities disposed on an outer surface stent pattern of the inner tubular member such that the cavities are located on the plurality of cylindrical elements; and a radiopaque coating affixed in the plurality of cavities in which the coating is formed by deposition of a radiopaque material.

18. The stent of clam 17, further comprising channels connecting the plurality of cavities with the body lumen.

19. The stent of claim 17, further comprising a radioactive coating affixed in the plurality of cavities in which the coating is formed by deposition of a radioactive material.

20. The stent of claim 17, further comprising a coating including a therapeutic substance affixed in the plurality of cavities in which the coating is formed by deposition of the therapeutic substance.

21. The stent of claim 17, wherein the radiopaque coating includes a radioactive material and wherein the coating is formed by simultaneous deposition of the radiopaque material and a radioisotope.

* * * * *

UNITED STATES PATENT AND TRADEMARK OFFICE
CERTIFICATE OF CORRECTION

| | | |
|---|---|---|
| PATENT NO. | : 6,641,607 B1 | Page 1 of 3 |
| APPLICATION NO. | : 09/753294 | |
| DATED | : November 4, 2003 | |
| INVENTOR(S) | : Syed F. A. Hossainy et al. | |

It is certified that error appears in the above-identified patent and that said Letters Patent is hereby corrected as shown below:

Title page, figure at bottom, make same changes as indicated above for FIG. 5 on Drawing Sheet 2 of 4 as shown on attached title page.

Drawing sheet 2 of 4, FIG. 4, change "10" to read --40--, "20" to read --44--, "25" to read --45--, "30" to read --42--, and a three sets of parallel lines, lead lines and --48-- as shown on attached Drawing sheet 2 of 4

Drawing sheet 2 of 4, FIG. 5, change "10" to read --40--, "20" to read --44--, and "30" to read --42--.

Column 18, line 52, claim 15, change "an", to read --and--.

Signed and Sealed this

Fourth Day of September, 2007

JON W. DUDAS
*Director of the United States Patent and Trademark Office*

(12) United States Patent
Hossainy et al.

(10) Patent No.: US 6,641,607 B1
(45) Date of Patent: Nov. 4, 2003

(54) DOUBLE TUBE STENT

(75) Inventors: Syed F. A. Hossainy, Fremont, CA (US); Shamim M. Malik, Temecula, CA (US); Steven Wu, Santa Clara, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 183 days.

(21) Appl. No.: 09/753,294

(22) Filed: Dec. 29, 2000

(51) Int. Cl.$^7$ .............................................. A61F 2/06
(52) U.S. Cl. .......................... 623/1.15; 623/1.44; 623/1.42
(58) Field of Search ........................... 623/1.13, 1.15, 623/1.16, 1.34, 1.14, 1.18–1.22

(56) References Cited

U.S. PATENT DOCUMENTS

| | | |
|---|---|---|
| 3,105,492 A | 10/1963 | Jeckel |
| 3,868,956 A | 3/1975 | Alfidi et al. |
| 3,993,078 A | 11/1976 | Bergentz et al. |
| 4,130,904 A | 12/1978 | Whalen |
| 4,718,907 A | 1/1988 | Karwoski et al. |
| 4,816,339 A | 3/1989 | Tu et al. |
| 4,879,135 A | 11/1989 | Greco et al. |
| 4,892,539 A | 1/1990 | Koch |
| 4,902,289 A | 2/1990 | Yannas |
| 4,986,831 A | 1/1991 | King et al. |
| 5,024,671 A | 6/1991 | Tu et al. |
| 5,037,377 A | 8/1991 | Alonso |
| 5,047,050 A | 9/1991 | Arpesani |
| 5,059,166 A | 10/1991 | Fischell et al. |
| 5,062,829 A | 11/1991 | Pryor et al. |
| 5,064,435 A * | 11/1991 | Porter .................... 623/23.7 |
| 5,078,736 A | 1/1992 | Behl |
| 5,084,065 A | 1/1992 | Weldon et al. |
| 5,100,429 A | 3/1992 | Sinofsky et al. |
| 5,104,403 A | 4/1992 | Brotzu et al. |
| 5,116,360 A | 5/1992 | Pinchuk et al. |
| 5,156,623 A | 10/1992 | Hakamatsuka et al. |
| 5,163,951 A | 11/1992 | Pinchuk et al. |
| 5,163,958 A | 11/1992 | Pinchuk |
| 5,176,617 A | 1/1993 | Fischell et al. |
| 5,180,366 A | 1/1993 | Woods |
| 5,192,311 A | 3/1993 | King et al. |
| 5,197,977 A | 3/1993 | Hoffman, Jr. et al. |
| 5,234,457 A | 8/1993 | Anderson |
| 5,236,446 A | 8/1993 | Dumon |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,302,168 A | 4/1994 | Hess |
| 5,354,329 A | 10/1994 | Whalen |
| 5,356,433 A | 10/1994 | Rowland et al. |
| 5,370,682 A | 12/1994 | Schmitt |
| 5,380,299 A | 1/1995 | Fearnot et al. |
| 5,382,259 A | 1/1995 | Phelps et al. |

(List continued on next page.)

FOREIGN PATENT DOCUMENTS

WO    WO 98/23228    6/1998

Primary Examiner—David H. Willse
Assistant Examiner—Hieu Phan
(74) Attorney, Agent, or Firm—Fulwider Patton Lee & Utecht, LLP

(57) ABSTRACT

A stent or intraductal medical device manufactured from a tubular member having an inner tube tightly fitted into an outer tube is provided. Microdepots may be formed on the outer surface of the inner tube, and may contain radioactive, radiopaque or therapeutic substances. A method for manufacturing such a medical device or stent is also described. The material to be deposited on the inner tube may be deposited on the inner tube by dipping or immersion, or the material may be applied to the inner tube using microinjection or electrodeposition. The material to be deposited may be applied to cavities or microdepots formed in the outer surface of the inner tube. Excess material may be removed from the inner tube by centrifugation or shaking, and the material to be deposited may be heated to bond the material to the surface of the microdepots on the inner tube.

21 Claims, 4 Drawing Sheets